United States Patent [19]
Akasaka et al.

[11] Patent Number: 5,785,650
[45] Date of Patent: Jul. 28, 1998

US005785650A

[54] MEDICAL SYSTEM FOR AT-HOME PATIENTS

[76] Inventors: Noboru Akasaka, 1-22-4-305, Nakaikegami, Ohta-ku, Tokyo, Japan; Masanori Kurosawa, 15-6,Nakagome 3-chome, Saku-shi, Nagano-ken, Japan; Koji Akai, 1-20-20, Shichirigahama, Kamakura-shi, Kanagawa-ken, Japan

[21] Appl. No.: 694,689

[22] Filed: Aug. 9, 1996

[30] Foreign Application Priority Data

Aug. 9, 1995 [JP] Japan ................... 7-203369

[51] Int. Cl.⁶ ........................................ A61N 5/00
[52] U.S. Cl. ........................... 600/300; 128/904
[58] Field of Search .................... 128/630, 670, 128/671, 903, 904, 920–925; 600/300, 301, 483, 484, 513

[56] References Cited

U.S. PATENT DOCUMENTS

| | | | |
|---|---|---|---|
| 4,838,275 | 6/1989 | Lee | 128/904 X |
| 5,003,984 | 4/1991 | Muraki et al. | 128/904 X |
| 5,086,391 | 2/1992 | Chambers . | |
| 5,348,008 | 9/1994 | Bornn et al. | 128/904 X |
| 5,421,343 | 6/1995 | Feng . | |
| 5,441,047 | 8/1995 | David et al. | 128/670 |
| 5,462,051 | 10/1995 | Oka et al. | 128/630 |
| 5,553,609 | 9/1996 | Chen et al. | 128/630 |
| 5,579,775 | 12/1996 | Dempsey et al. | 128/903 X |

FOREIGN PATENT DOCUMENTS 2 717 332 9/1995 France .

*Primary Examiner*—John P. Lacyk
*Assistant Examiner*—Samuel Gilbert
*Attorney, Agent, or Firm*—Wenderoth, Lind & Ponack, L.L.P.

[57] ABSTRACT

By integrally providing a medical organization, via a communication network, with a variety of medical data measured from a patient staying at home, a medical system for at-home patients makes it possible to make an appropriate diagnosis from a long distance. The system is equipped with an improved emergency reporting unit. The system includes a plurality of home units set up at the homes of patients, one or more center units at the local medical organization, and a network interconnecting these units via communication lines. The medical data are transmitted from the home units to center units via interface units which correspond to various measurement apparatuses. The system also has an emergency reporting function based on vital signs of a patient.

12 Claims, 2 Drawing Sheets

MEDICAL SYSTEM FOR AT-HOME PATIENTS

BACKGROUND OF THE INVENTION

The present invention relates to a medical system for long-distance or remote care of a patient who is staying at home. In particular, the present invention relates to a medical system that includes a communication network between a local medical center and a client's home.

As the ratio of old people in the total population rapidly increases, a medical system for remote care of "at-home" patients is becoming increasingly desirable. In one prior art system, only some specific functions, such as receiving electrocardiogram data from a patient, can be performed. A patient can utilize such a prior art system while being at home. Such a prior art system allows data, such as blood pressure and electrocardiogram, to be automatically transmitted. Such a system also allows the patient to input personal data, such as his/her body weight, for example, via a keyboard at a communication terminal or to provide his/her answers to questions posed to the patient by the system. Further, a pendant-shaped apparatus is also known which, by being pulled by a patient when an emergency occurs, transmits an emergency notice signal to a medical center.

In order to provide at-home patients with medical care from a distance, such a medical system as proposed in the prior art is incorporated with functions characterized as follows. A measurement and communication function is provided for measuring electrocardiogram, blood pressure, and pulse count, wherein these measured medical data are transmitted via pulse-wave from a patient's home to a local medical center. A function for interfacing with various kinds of medical equipment is provided. The various kinds of medical equipment correspond to a plurality of symptoms appearing in patients, wherein the symptoms are obtained from the above medical data. A diagnosis/instruction function is provided in which a real time conversation can be conducted orally between a physician at the local medical center and each of the patients via on-screen input/output means. The system of the prior art also provides a better emergency alert function. However, the specific functions incorporated in the prior art medical care system are insufficient and thus further improvements are required. Therefore, such prior art systems are not widely utilized among medical organizations today.

SUMMARY OF THE INVENTION

An object of the present invention is to improve on the functions of the prior art medical system described above and to integrate all the necessary functions into a single system, whereby "at-home" patients are provided with better medical care. It is also an object of the present invention to make the use of such a medical system more widespread and to ultimately establish a medical institution by which the lives of at-home patients will be enhanced as their medical conditions are monitored at a distance in an appropriate manner.

The above and other objects of the present invention are accomplished by a system which includes a network of home units and at least one center unit. The home units are located in patients' homes and the at least one center unit is located at a medical institute. The medical center functions as a local center for the at-home patients in the community. Each of the home units, as well as the center unit, include a computer equipped with a high speed microprocessor (CPU) and an appropriate modem which allows bi-directional communication between each of the home units and the medical center, thus allowing information to be exchanged on a real time basis. Therefore, a physician or a nurse can provide the at-home patient with an instruction suitable to his/her specific bodily condition based on the medical information acquired via the system.

Also, by using the system according to the present invention, it is possible, depending on the patient's actual requirements, to keep a vital sign detector mounted on the patient's body which monitors, from a distance, his/her vital signs on a twenty-four hour basis. Upon detection of any interruption of the vital signs, the CPU within the home unit assumes that an abnormal condition with respect to the patient's body has occurred and immediately transmits an alert signal to the center unit. This function makes it possible for the medical professionals at the medical center to immediately respond to such an urgent situation in a more certain manner than the prior art pendant shaped apparatus described above.

In the system of the present invention, a home unit can, collectively rather than individually, obtain basic medical data such as blood pressure, pulse wave, electrocardiogram, cardiac sound, pulmonary sound, body temperature, and transmit such data, via communication lines, to the center unit at the medical center, where physicians, by monitoring the received data, can provide a proper diagnosis for the distant patient.

DETAILED DESCRIPTION OF A PREFERRED EMBODIMENT

Figure 1:
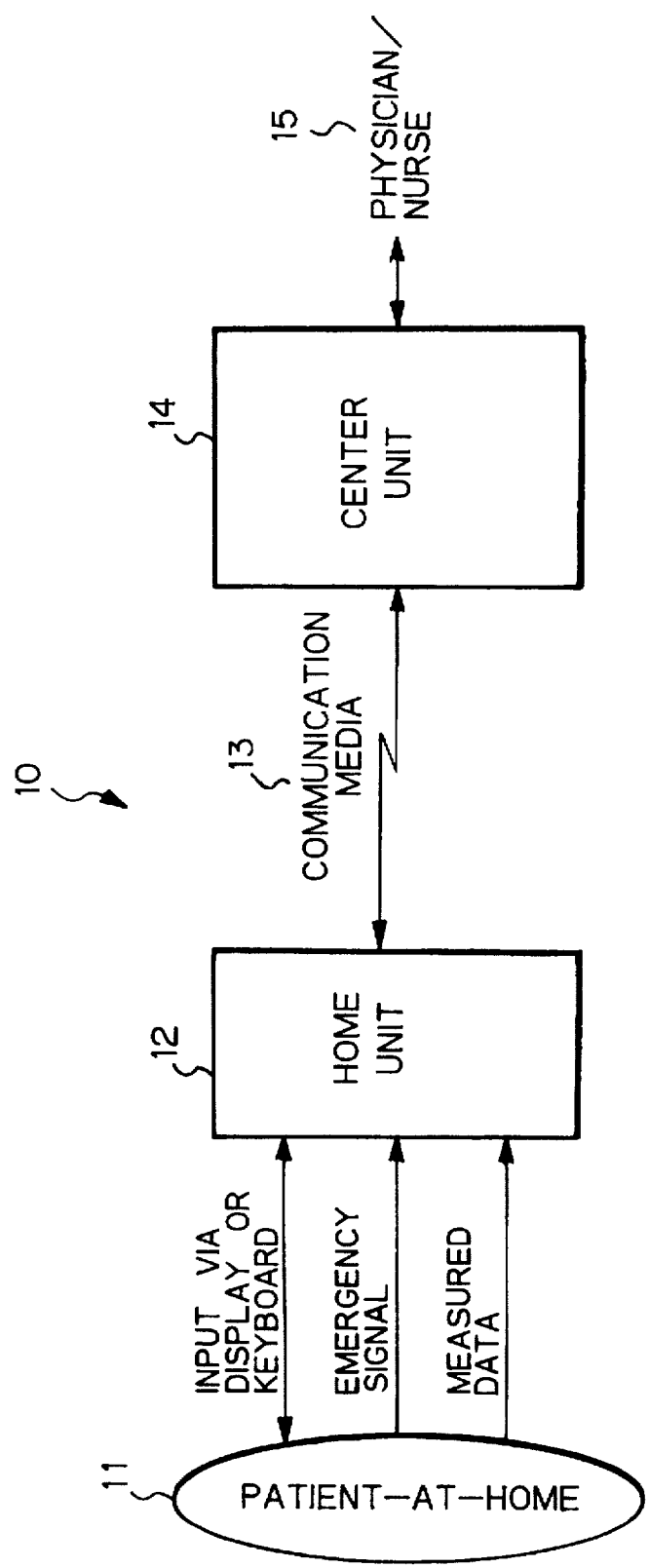
FIG. 1 a block diagram of the medical system for at-home clients, in accordance with the present invention.

A preferred embodiment of the present invention will now be described by referring to the drawings. Referring to FIG. 1, an apparatus 12 set up at a client's home (hereinafter referred to as a "home unit") and an apparatus 14 set up at a local medical center (hereinafter referred to as "center unit") are interconnected via a communication line 13 making bi-directional data communication possible. Each of the home unit 12 and the center unit 14 has a computer capable of providing on-line communication between them. The at-home patient at the home unit 12 and a physician or nurse 15 at the center unit 14 are able to input necessary data into the computer of their respective units via an input device such as a touch panel or a keyboard. A diagnosis and/or instruction via a real-time conversation over the line is also possible. Since a typical at-home patient 11 of this kind may not be sufficiently computer literate, almost all the functions of the home unit 12, including those for transmitting and receiving, are automated and the data which is input by the at-home patient 11 is minimized as much as possible.

Communication between the home unit 12 and the center unit 14 may be initiated at either end. For example, an alert notice and measured bio-medical data can be transmitted from the home unit 12, or medical personnel at the local medical center can themselves check and, if necessary, collect data from the home unit via the center unit 14.

Figure 2:
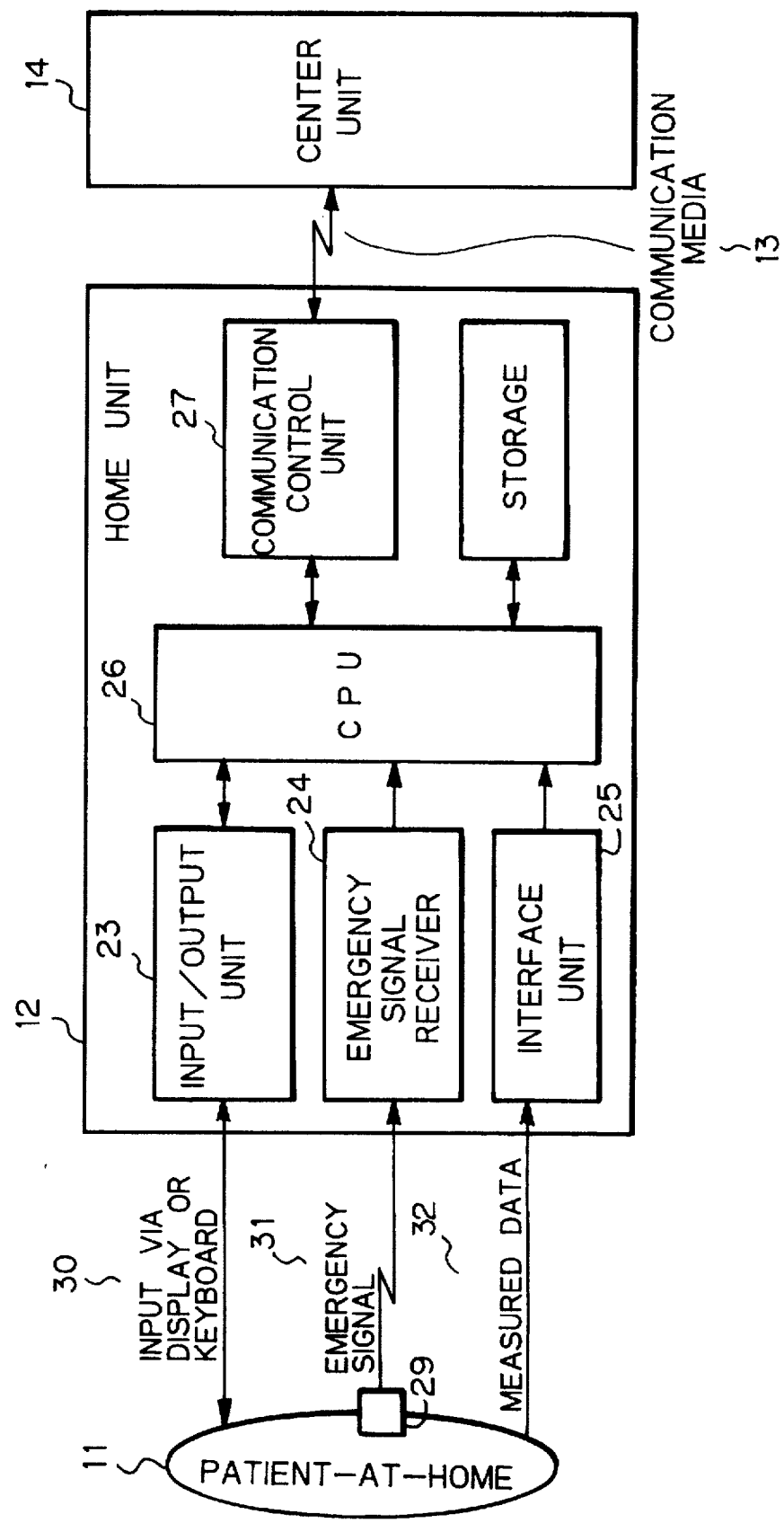
FIG. 2 a more detailed block diagram of a home unit in the medical system for at-home clients, in accordance with the present invention.

In FIG. 2, the home unit 12 of the system is illustrated in a more detailed manner. The elements shared by FIGS. 1 and 2 are identified with the same reference numerals. Detected medical data such as blood pressure, pulse wave, electrocardiogram, cardiac sound, pulmonary sound, and body temperature of an at-home patient are input into the home unit 12 through an input/output unit 23. The at-home patient 11 is only asked to put on a blood pressure meter or electrodes of an electrocardiograph and turn on the switch, for example, to measure and automatically transmit to the center unit 14 his/her blood pressure or electrocardiogram. On the display screen at the center unit 14, these transmitted and received data are displayed with the identification number of the at-home patient 11. This data can conveniently be relied upon by a physician or nurse 15 in deciding what measures, if any, should be taken.

Medical data for a large number of at-home patients, e.g., patients who live in the community serviced by a particular medical center, are stored in an external storage device attached to the computer of the center unit 14 of the medical center. Such medical data include biographical and newly measured data of those patients. When a medical professional makes a diagnosis on the basis of the data automatically transmitted from a home unit 12 and received at the center unit 14, he/she can display medical data in one or more desired windows on the display screen by retrieving databases stored in the external storage device. The data thus retrieved may then be referred to and relied upon by the doctor or nurse. The medical data automatically transmitted from the home unit 12 of a specific at-home patient 11 to the center unit 14 will be stored in a file specifically assigned to the patient within the database.

The system of the present invention, unlike the prior art systems, is not limited to specific groups of data with respect to the obtaining and transmission of data. Rather, the present invention allows for the collection and automatic transmission of a variety of data such as blood pressure, pulse wave, electrocardiogram, cardiac sound, pulmonary sound, and body temperature of an at-home patient 11. Since a diagnosis by a physician can only be made depending upon a plurality of factors collected, it is preferable to collect as many kinds of medical data from the patient as possible. If conventional measurement apparatuses are employed to measure these data, the interface unit 25 provides gives a good interface between the home unit 12 and a measurement apparatus. It is also possible to use a measurement apparatus dedicated to the home unit 12.

Referring to FIG. 2 again, the interface unit for receiving medical data from the patient 11 receives data such as blood pressure, pulse wave, electrocardiogram, cardiac sound, pulmonary sound, and body temperature from an at-home patient 11, converts the data into digital form if necessary, and transmits the resultant data in an appropriate format to the center unit 14 via the communication control unit 27. This communication is bi-directional and may be initiated both at the home unit 12 and at center unit 14. The interface unit 25 is configured to automatically adjust the signal level with an input signal so that a variety of medical data can be obtained. The interface unit 25 may be replaced with another interface unit if a medical measurement device which requires an interface unit with a different interface protocol is to be connected.

Even with a prior art system, it was already possible for medical data such as blood pressure, pulse wave, electrocardiogram, and body temperature, which are commonly treated as numerical data, to be measured and transmitted. However, these types of data were transmitted individually and independently. In contrast to that, the system of the present invention is further provided with a function that allows a physician at a local medical center to, remotely or via a communication network, listen to the cardiac and/or pulmonary sound of a patient. Although this is a very common routine performed in a face-to-face diagnosis, and is regarded as being necessary even in the medical system at home, this function has not been implemented with prior art systems.

Each of the home units 12 and the center unit 14 may have a microphone/speaker function by which a real time bi-directional conversation will be possible between an at-home patient 11 and a physician/nurse 15 at a local medical center. The participants of the conversation need only to face their own unit 12 or 14 and proceed with the conversation while watching the medical data and/or graphs drawn therefrom which are displayed on the screen. The physician/nurse 15 may, on a real time basis, ask questions and give instructions to the at-home patient. The local medical center often has a plurality of center units 14 interconnected to one another so that the center is capable of coping with a large number of at-home patients 11 who live in the community and have entered into a contract with the medical center. Therefore, each at-home patient 11 does not have to wait as long before he/she can talk with a physician/nurse 15. Or instead of a real time conversation with a physician/nurse 15, comments on the patient's medical data by a physician/nurse 15 may be transmitted via a center unit 14 to a home unit 12. The comments can be stored in a storage device, such as a RAM, and output as audio data at the moment they are desired by the at-home patient 11. By using this function, both the physician/nurse 15 and the at-home patient 11 may be able to effectively transmit and receive medical instructions without taking too much of the other's time.

With respect to an emergency notice function for reporting to the local medical center the occurrence of any urgent situation with respect to an at-home patient's body, the present invention is based on a fail-safe principle and has been significantly improved in terms of reliability over the prior art system. Signals from an emergent abnormality detector 29 mounted on the at-home patient 11 are received by an emergent signal receiver unit 24 of home unit 12, and are interpreted by CPU 26. Signals reporting an occurrence of an emergency will be transmitted to a center unit 14. The center unit 14 then recognizes the occurrence of the emergency situation by receiving such signals and immediately notifies the physicians/nurses 15 and the medical center itself of the situation by generating a buzzer sound, for example, from a speaker. At the same time, the center unit 14 transmits an acknowledge signal to the home unit 12 notifying that the medical center has recognized an occurrence of an emergency situation on the patient's body. If the emergent signal from the home unit 12 had been the result of some failure and no emergencies have actually occurred, the home unit 12 then transmits to the center unit 14 a signal notifying that the prior notice was due to a failure rather than an actual emergency.

In order to realize the above-mentioned emergency notification function, a small portable apparatus is worn on the patient's body and this apparatus detects the vital signs of the patient which show that the patient is alive. A typical vital sign is the pulse at the patient's wrist. The vital sign detector incorporates a small-sized battery and continues to transmit a constant electrical signal as long as the detector can detect normal vital signs from the patient's body. If the patient stays within a predetermined area, the home unit 12 can receive the electrical signal representative of the vital signs. As long as the home unit continues to detect the electrical signal, which confirms that the patient is alive, the home unit 12 does not generate any response. However, once the detection of the signal is discontinued, the home unit 12 will automatically transmit an emergent signal to the center unit 14 without investigating the reason for the discontinuance. The home unit 12 thereby notifies the medical personnel of an occurrence of an emergent situation. A discontinuance of the electrical signal may be due to reasons other than an abnormality in the patient's body, such as electrical or mechanical failures of the detector. However, any discontinuance will be unconditionally reported to the center unit 14 as an occurrence of an emergency as a result of the fail safe principle. On receiving such an emergent signal, the center unit 14, without delay, takes necessary measures, namely making a phone call to see if the patient answers the phone, or other steps to attempt to find out the actual situation.

The prior art pendant-shaped emergency reporting apparatus may not function if the patient is too sick or too weak to pull down the pendant. Thus in a situation where the at-home patient 11 is suddenly incapacitated or so sick that he/she cannot pull down the pendant-shaped detector to transmit the emergency signal, no signals are generated. The emergency reporting apparatus in accordance with the present invention, however, is configured in such a manner that the home unit 12 always regards the situation as being an emergency once the electrical signal is discontinued for any reason. Thus reliability is significantly improved compared to the prior art apparatus.

In order for this fail-safe function to operate more efficiently, the emergency notification function can be temporally suspended by setting the home unit 12 in an absent mode so that a discontinuance of the electrical signal does not necessarily cause an emergency signal to be generated.

The detected vital signs can also be, depending on the condition of the patient, the arterial oxygen saturation ($SpO_2$) or expired terminal carbon dioxide ($ETCO_2$). In such a case, the recognition mechanism of the emergency signal will be the same as when detecting the patient's pulse, the only difference being in the detector.

In accordance with the present invention, a variety of physical data can be integrally transmitted to a medical organization without any difficulty, thus making it possible for a physician/nurse to provide an at-home patient with remote monitoring and diagnosis. The present system can also provide at-home patients, the number of which are expected to increase, with better and more efficient diagnoses than prior art systems. Because of the bi-directional communication of this system, at-home patients may receive real-time diagnoses based on their own bodily data via communication media while staying at home.

Further, using the emergency reporting function of this system, the medical organization can be rapidly and reliably notified of emergency situations of at-home patients, thereby making appropriate medical treatment possible at an early stage, as well as helping the patients survive such emergencies. Such early treatment also prevents patients from ending up in a serious condition, which may save on extra medical expenses, and with the further result that an efficient allocation of medical resources can be acquired.

While several embodiments of the present invention have been shown and described, alternate embodiments will be apparent to those skilled in the art and are within the intended scope of the present invention. Therefore, the invention is to be limited only by the following claims.

What is claimed is:

1. A medical system for at-home patients comprising:
   a home unit which is located at a home of an at-home patient and which includes a computer with a communication capability;
   a center unit which is located at a medical organization and which includes a computer with a communication capability;
   a network interconnecting said home unit and said center unit;
   medical data detection means for detecting a plurality of medical data from the at-home patient;
   an interface unit, in said home unit, which corresponds to said medical data detection means;
   home unit transmitting means, in said home unit, for transmitting the plurality of medical data, detected by said medical data detection means, to said center unit, via said interface unit;
   center unit transmitting means, in said center unit, for transmitting to said home unit instructions based on the plurality of medical data transmitted by said home unit transmitting means; and
   means, in said home unit, for detecting emergency condition information, separate from said medical data, of the patient and for transmitting to said center unit an emergency signal based on said emergency condition information, said emergency signal being separate from the medical data.

2. A medical system for at-home patients as claimed in claim 1, wherein said means for detecting emergency condition information is separate from said medical data detection means.

3. A medical system for at-home patients as claimed in claim 2, further comprising:
   vital sign detection means, separate from said medical data detection means, for detecting a vital sign of the at-home patient and for continuously transmitting a constant electrical signal to said home unit while the vital sign is detected;
   wherein said means for detecting emergency condition information continuously detects said constant electrical signal and, when said constant electrical signal is discontinued, said means for detecting emergency condition information transmits said emergency signal to said center unit.

4. A medical system for at-home patients as claimed in claim 3, wherein said means for detecting emergency condition information further comprises:
   means for transmitting a notification signal to said center unit if said emergency signal has been transmitted to said center unit and if there is no medical emergency.

5. A medical system for at-home patients as claimed in claim 3, further comprising:
   absent mode setting means for setting said means for detecting emergency condition information such that said means for detecting emergency information does not transmit said emergency signal when said constant electrical signal is discontinued.

6. A medical system for at-home patients as claimed in claim 3, wherein the vital sign comprises a pulse of the at-home patient.

7. A medical system for at-home patients as claimed in claim 3, wherein the vital sign comprises an arterial oxygen saturation ($Spo_2$) of the at-home patient.

8. A medical system for at-home patients as claimed in claim 3, wherein the vital sign comprises an expired terminal carbon dioxide ($ETCO_2$) of the at-home patient.

9. A medical system for at-home patients as claimed in claim 1, further comprising:

sound detecting means for detecting sound waves from the at-home patient, wherein the sound waves are useful in diagnosis of the at-home patient, and for transmitting the sound waves to said center unit.

10. A medical system for at-home patients as claimed in claim 9, wherein the sound waves comprise a cardiac sound.

11. A medical system for at-home patients as claimed in claim 9, wherein the sound waves comprise a pulmonary sound.

12. A medical system for at-home patients as claimed in claim 1, further comprising:

storage means, in said home unit, for storing said instructions transmitted by said center unit transmitting means; and output means, operated by the at-home patient, for outputting said instructions from said storage means as audio data.

* * * * *